United States Patent [19]

Bossier et al.

[11] 4,431,847

[45] Feb. 14, 1984

[54] METHOD FOR REMOVING BROMINATED PHENOLIC WASTE

[75] Inventors: Joseph A. Bossier, Greenwell Springs; Julio J. Vega, Baton Rouge, both of La.

[73] Assignee: Ethyl Corporation, Richmond, Va.

[21] Appl. No.: 402,931

[22] Filed: Jul. 29, 1982

[51] Int. Cl.$^3$ ............................................. C07C 37/68
[52] U.S. Cl. ..................................... 568/755; 568/726; 568/725; 568/776; 568/779
[58] Field of Search ............... 568/725, 726, 755, 776, 568/779

[56] References Cited

U.S. PATENT DOCUMENTS

| | | | |
|---|---|---|---|
| 3,182,088 | 5/1965 | Hennis | 568/726 |
| 3,546,302 | 12/1970 | Asadorian et al. | 568/726 |
| 3,929,907 | 12/1975 | Janson et al. | 568/726 |
| 4,160,112 | 7/1979 | Levek et al. | 568/776 |
| 4,180,684 | 12/1979 | Kleinschmit et al. | 568/725 |

FOREIGN PATENT DOCUMENTS

| | | | |
|---|---|---|---|
| 706433 | 3/1965 | Canada | 568/726 |
| 1031500 | 6/1966 | United Kingdom | 568/726 |
| 341790 | 7/1972 | U.S.S.R. | 568/726 |

*Primary Examiner*—Werren B. Lone
*Attorney, Agent, or Firm*—Donald L. Johnson; John F. Sieberth; Teresa M. Stanek

[57] ABSTRACT

A process for forming a substantially insoluble solid polymer from halogeneated phenolic compounds dissolved in a liquid medium using an oxidizing agent. NaOCl and NaOBr are used as oxidizing agents to initiate the polymerization reaction among the halogenated phenolic compounds. The polymer precipitates from the system to form a claylike solid. The solid is environmentally safe and may be disposed of in a sanitary landfill.

29 Claims, No Drawings

METHOD FOR REMOVING BROMINATED PHENOLIC WASTE

BACKGROUND OF THE INVENTION

1. Field of the Invention

This invention relates to a method for polymerizing halogenated phenolic compounds. More particularly, this invention relates to a method for removing brominated phenolic compounds from a waste stream. The brominated phenolic compounds are polymerized to obtain a fine, innocuous solid which can be easily separated from the waste stream.

2. Description of the Prior Art

Tetrabromobisphenol-A ("TBBPA") also known as 4,4'-isopropylidenebis[2,6-dibromophenol] is a bromine-containing flame-retardant monomer for plastics. TBBA is used in epoxy resins for the copper-clad electronic circuit board market. TBBPA is also used in polycarbonate, polybutylene terephthalate and unsaturated polyester resins.

The preparation of tetrabromobisphenol-A (TBBPA) by brominating bisphenol-A ("BPA") in a solvent is well-known. The brominating agent typically is bromine or a bromine-chlorine mixture. The solvent can be an alcohol, aqueous acetic acid, a non-polar solvent or a two-phase water-organic system.

One method of producing TBBPA is described in U.S. Pat. No. 3,182,088. It involves the bromination of BPA in an anhydrous methanol solvent. Following bromination, TBBPA is crystallized by adding water. The crystals are filtered, washed on the filter to remove impurities and then dried. Generally, an attempt is made to recover the sodium bromide in the waste stream for its bromine value.

If a methanol solvent is used, as exemplified in U.S. Pat. No. 3,182,088, the excess solvent may be recovered upon completion of the reaction using a methanol distillation column. Depending on the process conditions selected, a variety of compounds are present in the aqueous column bottoms. If the methanol distillation is carried out under caustic conditions using an alkali metal hydroxide such as NaOH at a pH of 13–14, the components present in the distillation column bottoms include sodium salts of brominated phenolics, residual methanol, sodium bromide, trace amounts of acetone, NaOH, and the like. If an alkali metal hydroxide is not added prior to the distillation, then the waste stream is acidic and may be neutralized with a base. If NaOH is used then sodium salts of brominated phenolic compounds and sodium salts of polybrominated bisphenol-A are present in the waste stream. The organic bromides found in the distillation column waste stream are primarily polyhalogenated phenolics such as tetrabromobisphenol-A, tribromobisphenol-A and tribromophenol. The average composition of the distillation column bottoms is quite variable. A typical composition for a basic distillation is 92.7–95.4 weight percent water, less than 0.2 weight percent methanol, 0.9–1.1 weight percent brominated phenolic compounds, weight percent NaBr and 0.5–1.0 weight percent NaOH.

The process of the present invention is designed to remove polyhalogenated phenolic compounds from waste streams such as those described above. Treatment of these compounds by the practice of the present invention results in the formation of an insoluble solid polymer that is easily removed by filtration. The precipitate removed is an inert, non-hazardous, clay-like polymer that is suitable for disposal in a sanitary land-fill. At the present time polybrominated phenols are suspected carcinogens but the polybrominated bisphenols are not. The polybrominated phenolic compounds present a waste disposal problem because of their potential impact on health and the environment. It is beneficial to alter or modify the polybrominated phenols in an economically feasible manner to obtain non-hazardous material. The non-hazardous material is then easily disposed of in a landfill site.

A prior method of handling waste stream containing brominated phenolic impurities involved precipitation and incineration. After filtering off the TBBPA, most of brominated phenolic impurities were precipitated from the aqueous acidic filtrate by distilling out most of the methanol; usually, in a flash pot ahead of the final methanol recovery distillation column. The precipitated solids were sticky and hard to handle but they could be dissolved in methanol. Since some of the brominated phenolic wastes are suspected to be carcinogens, disposal of the methanol solution was costly. A waste incerator was used followed by an exhaust gas scrubber. The present process can be applied to the removal of above brominated phenolic waste from the methanol solution without the necessity of incineration.

It has now been discovered that a waste stream containing sodium salts of polybrominated phenolic compounds can be treated with an oxidizing agent such as sodium hypochlorite (NaOCl) or sodium hypobromite (NaOBr). These oxidizing agents initiate a polymerization reaction among the polybrominated phenolic and polybrominated bisphenolic compounds in the waste stream. The polymerized product is a fine, innocuous, insoluble solid that does not present health or environmental problems. The solid waste product settles rapidly and therefore may be readily separated from the aqueous waste stream for disposal.

SUMMARY OF THE INVENTION

According to the present invention, polyhalogenated phenolic compounds can be removed from a liquid medium having a pH within the range of about 7 to 14 by the addition of an oxidizing agent such as the combination of NaOH and either $Cl_2$ or $Br_2$. The NaOH and $Cl_2$ or $Br_2$ react in situ to form NaOCl or NaOBr. The NaOCl or NaOBr initiate a polymerization reaction among polyhalogenated phenolic compounds present in the liquid reaction medium. The resulting polyether precipitates from the system as a fine, innocuous solid that is readily disposed of in an environmentally acceptable manner.

DESCRIPTION OF THE PREFERRED EMBODIMENTS

A preferred embodiment of the present invention is a process for forming a substantially insoluble solid polymer from halogenated phenolic compounds dissolved in a liquid medium where the liquid medium has a pH within the range of about 7 to 14. This process comprises adding an oxidizing agent to the liquid medium in an amount sufficient to form a solid polymer, and reacting at a temperature of about 30° F. to about 300° F. The polymer may be separated from the liquid medium by conventional methods.

The halogenated phenolic compounds are preferably brominated phenolic compounds. More preferably, the brominated phenolic compounds are selected from the group consisting of tetrabromobisphenol-A, tribromophenol and the like.

A more preferred embodiment of the present invention is an improvement in a process for making tetrabromobisphenol-A, said process comprising dissolving bisphenol-A in methanol, adding bromine to the liquid in an amount sufficient to convert said bisphenol-A to tetrabromobisphenol-A, optionally removing by-product methyl bromide, adding water to precipitate said tetrabromobisphenol-A, separating the precipitated tetrabromobisphenol-A from the reaction mixture, adjusting the pH of the liquid phase to 7–14, distilling the liquid phase to remove a substantial portion of methanol thereby obtaining distillation column bottoms containing minor amounts of the sodium salts of brominated phenolic contaminants. According to the improvement said contaminants are converted to an insoluble solid polymer by a procedure comprising adding an oxidizing agent selected from the group consisting of alkali metal hypochlorites, alkali metal hypobromites and the combination of alkali metal hydroxide and halogen selected from chlorine, bromine and mixtures thereof in an amount sufficient to convert said brominated phenolic contaminants to said insoluble solid polymer.

Optionally, the methanol may be distilled from the liquid phase after removal of the precipitated TBBPA without neutralization. However, this will cause some of the brominated phenolic contaminants to precipitate in a sticky form. Hence, this is not the preferred mode. When done in this manner the liquid phase remaining after distilling out methanol is neutralized with caustic to be in the range of 7–14, more preferably 8–12 and then the dissolved contaminants are converted to an insoluble solid polymer as in the more preferred embodiment.

A suitable method for making tetrabromobisphenol-A (TBBPA) is described in U.S. Pat. No. 3,182,088 incorporated herein by reference. Bisphenol-A is dissolved in methanol and bromine is added to the solution at temperatures up to reflux. Stoichiometry requires 4 moles of bromine but a slight excess is used to assure complete bromination. By-product HBr reacts with methanol to form methyl bromide which is very volatile (b.p. 3.5° C.) and distills off and is recovered. Water is added in an amount sufficient to precipitate the TBBPA which is removed by filtration leaving an acidic filtrate containing water, methanol and various bromine compounds. The removal of brominated phenolic contaminants from this liquid waste stream is a principal object of the present invention.

In a preferred embodiment, the methanol in the liquid waste stream is removed prior to removal of the brominated phenolic waste. This is accomplished by distillation leaving residual distillation column bottoms.

Following the bromination of bisphenol-A in the methanol solvent the reaction mixture is acid because of the formation of HBr by-product. Prior to removal of the brominated phenolic waste the system must have a pH of 7–14. This neutralization can take place anytime after TBBPA precipitation and removal of the TBBPA product. The neutralization can occur prior to distilling out the methanol or after distilling out the methanol. Preferably, sufficient base is added prior to the distillation of the methanol to at least neutralize the system. This will minimize corrosion problems and prevent the precipitation of sticky brominated phenolic compounds. Further pH adjustment can occur after methanol distillation. Any base can be used for the neutralization. Preferably an alkali metal hydroxide such as NaOH or KOH is used.

Following neutralization and methanol distillation in whichever sequence they are carried out, the resulting column bottoms are subjected to addition of an oxidizing agent to cause the brominated phenolics to form an insoluble solid polymer.

The oxidizing systems intended for use in the present invention are among those well-known in the art. For example, polymers of moderate molecular weight may be formed by oxidizing halophenols with ferricyanide. Alternately, dichromate and permanganate may also be used as oxidizing agents in carrying out the process of the present invention. Representative oxidizing agents include $K_2Cr_2O_7$, $KMnO_4$, $K_3Fe(CN)_6$ and the like. The preferred oxidizing system intended for use in the present invention is an alkali metal hypohalite such as NaOCl, KOBr, KOCl or NaOBr. The addition of an alkali metal hydroxide such as NaOH or KOH and a halogen such as $CL_2$, $Br_2$ or a combination of $Cl_2$ and $Br_2$ forms NaOCl, KOBr or mixtures thereof in the reaction system. It is the alkali metal hypohalite such as NaOCl or NaOBr that initiates the polymerization reaction. Therefore, the alkali metal hypohalite may be pre-formed and added directly to the reaction system and the polymerization reaction will proceed in the same manner as when the alkali metal hydroxide and halogen are added separately. The preferred oxidant to be used in the practice of the present invention is either an aqueous solution of NaOCl containing excess caustic or the combination of NaOH and chlorine.

The amount of oxidizing agent used in the process should be an amount sufficient to convert the brominated phenolic contaminants to a substantially insoluble solid polymer. The optimum amount can readily be determined in a few experiments. A useful range is from about 0.06 to about 10.0 parts by weight of oxidizing agent for each part by weight of brominated phenolic compounds. Preferably, about 0.1 to about 1.0 part by weight of oxidizing agent is used for each part by weight of brominated phenolic compound. More preferably, there is approximately 0.35 to 0.75 part by weight of oxidizing agent, such as NaOCl or NaOBr used for each part of brominated phenolic compounds present in the distillation column bottoms.

Preferably, the reaction is conducted in an aqueous system, however, the reaction is not limited to an aqueous system. The polymerization reaction of the present invention may be carried out in an organic solvent. Preferred organic solvents include methanol and ethyl acetate.

As stated above, the most preferred reaction medium in which to conduct the conversion of polyhalogenated phenolic compounds to insoluble solid polymers is an aqueous medium. When this conversion is used as a means of removing brominated phenolic contaminants from a waste stream of a TBBPA process, as described herein, there is usually sufficient aqueous medium in the distillation column bottoms after methanol distillation such that no additional water is required. However, if desired, additional water can be added to the distillation column bottoms.

The pH of the reaction media is preferably adjusted to be within the range of about 7 to about 14. More preferably, the pH is within the range of about 8 to about 12. Even more preferably the pH is within the range of 9–11. The pH of the reaction medium directly influences the amount of oxidizing agent, such as NaOCl or NaOBr, needed to completely polymerize all of the polyhalogenated phenolic compounds found in the reaction medium. More NaOCl or NaOBr is required for a high pH system than for a lower pH system. That is, more NaOCl or NaOBr is required at a pH of 13-14 than at a pH of 11.

At a pH of 11 the polymer formed by the practice of the present invention generally precipitates out of solution immediately upon addition of the NaOCl or NaOBr oxidizing agent. For a system with a pH of from 12-13, the polymer tends to form several minutes after the NaOCl or NaOBr is added. Beyond a pH of approximately 13, the polymer appears at a much slower rate. It is speculated that the slower precipitation is probably caused by the high solubility of the monomers and small chain polymers in the high pH system.

Generally, the term pH is used when referring to an aqueous system. When referring to a non-aqueous system, it is possible to state the relative alkalinity of the non-aqueous system in terms of alkalinity equivalent to a certain weight percent NaOH. In a non-aqueous system the alkalinity of the system is preferably equivalent to about $10^{-7}$ to about $10^1$ weight percent NaOH. More preferably, the alkalinity is equivalent to about $10^{-6}$ to about $10^{-2}$ weight percent NaOH. Even more preferably, the alkalinity is equivalent to about $10^{-5}$ to about $10^{-3}$ weight percent NaOH.

The solids produced by fast precipitation at a pH of 11 were found to be slightly soluble in solvents such as tetrahydrofuran, dimethylsulfoxide and methanol. Solids produced in the slow precipitation system at a pH of 13-14 were found to be completely insoluble in the solvents listed above. It is speculated that the high pH system allows the formation of longer and more organized polymer chains which are less soluble.

The reaction is conducted at a temperature high enough to cause the polymerization to proceed, yet not so high as to adversely affect the course of the reaction. The reaction temperature generally ranges from about 30° F. to about 300° F. Preferably, the temperature ranges from about 70° F. to about 100°0 F.

It has been determined that more NaOCl or NaOBr is needed at higher temperatures. Approximately 22% more NaOH is needed at 125° F. and about 27% more is needed at 160° F. than at 100° F.

In general, the reaction is conducted under ambient pressures since these are most economical. However, reaction pressure is not critical. In general, vacuum or partial vacuum offers no material advantage. Elevated pressures up to 1000 psig or more can be utilized when it is desired to conduct the process at a temperature above the normal boiling point of one or more materials in the reaction mixture.

The reaction time is not critical, but depends to some extent on the inherent reactivity of the reactants and other reaction conditions employed. In general, reaction times of from seconds to a few hours are sufficient. However, if the amount of oxidizing agent, pH and temperature are carefully selected, within a matter of minutes a virtually complete polymerization of brominated phenolic compounds can be achieved.

The specific characteristics of the claylike polymer prepared in the manner taught by the present invention varies depending on the reaction conditions used. However, generally the particle size ranges from 1-20 microns with a mean particle size of 2-3 micron. The average molecular weight is in the range of 2600-2800.

Several methods are available to recover and dispose of the polymerized waste solids of the present invention. These methods include settling, centrifugation, filtration and adsorptive-bubble separation.

Adsorptive-bubble separation, oftentimes referred to as foam separation, is one of the preferred methods of recovering the waste polymer. This method is based on the selective adsorption or attachment of materials on the surface of gas bubbles passing through a solution or suspension. In most of the foam separation methods, the bubbles rise to form a foam or froth which carries the material off overhead. Thus, the material (desirable or undesirable) is removed from the liquid, and not vice versa as in filtration. Accordingly, the foaming methods appear to be particularly suited to the removal of small amounts of material from large volumes of liquid. If the material to be removed is not itself surface active, a suitable surfactant may be added to unite with it and attach or absorb it to the bubble surface so that it may be removed.

The most preferred method of waste solids recovery is filtration. Large volumes are readily handled with a vacuum filter, such as a rotary drum vacuum filter. A precoat of filter aid is generally preferred. Filtration done without precoat gives poor clarity and quick blinding of the cloth by solids. An example of a precoat is Dicalite ®476 perlite filter aid.

Although we do not wish to be bound by any theory because it is not necessary to understand the mechanism to successfully practice the invention, we believe that to initiate the polymerization reaction, halogenated phenolic compound is converted to a free radical to begin each of the polymer chains. Therefore, the amount of oxidizing agent added is not a catalytic amount but must be sufficient to generate a free radical for each linkage. Since in the TBBPA process the brominated phenols are present in the alkali metal hydroxide neutralized waste stream in the form of alkali metal salts and one bromine atom is lost during the addition of each linkage on the polymer chain, then for each mole of brominated phenol linked in the polymer chain, one mole of alkali metal bromide is formed. Some alkali metal bromide was already formed in the neutralization of HBr formed during the bromination of bisphenol-A. After removal of the solid polymer the alkali bromide rich aqueous waste stream may be processed by known procedures for bromine recovery.

The key feature of the present invention is the nonhazardous nature of the polymer produced. Rat feeding studies have been conducted on waste polymer from a TBBPA process. Acute oral and dermal toxicity test results indicate the waste is not a Poison B (DOT). The research record indicates an $LD_{50}$ (rat oral) of greater than 50 mg/kg and $LD_{50}$ (rabbit dermal) of greater than 200 mg/kg. The solid waste as taught by the present invention also failed to exhibit, by EPA standards, hazardous waste characteristics of ignitability, corrosivity, reactivity and EP (Extraction Procedure) toxicity.

Leachate tests were run according to EPA guidelines and the results are given in Table I. The extract obtained from applying the EPA Extraction Procedure (EP) did not contain contaminants in excess of the EPA limits.

TABLE I
Results of Leachate Tests with TBBPA Waste Polymer

| Substance | EPA Limits (ppm) | Analytical Results (ppm) |
|---|---|---|
| Arsenic | 5 | 0.004 |
| Barium | 100 | 0.05 |
| Cadmium | 1 | 0.05 |
| Chromium | 5 | 0.02 |
| Lead | 5 | 0.05 |
| Mercury | 0.2 | 0.006 |
| Selenium | 1 | 0.005 |
| Silver | 5 | 0.01 |
| Endrin | 0.02 | 0 |
| Lindane | 0.4 | 0.0016 |
| Methoxychlor | 10 | 0 |
| Toxaphene | 0.5 | 0 |
| 2,4,5-Trichlorophenoxy propionic acid | 10 | 0 |
| 2,4-Dichlorophenoxy acetic acid | 1.0 | 0 |

The following examples illustrate the process of polymerizing polyhalogenated phenolics according to the present invention. All parts are by weight unless otherwise stated. These examples are in no manner intended to limit the invention described.

EXAMPLE 1

Preparation of Tetrabromobisphenol-A

In a reaction vessel was placed 2000 parts methanol and 1000 parts of bisphenol-A. Bromine was fed over a 1 hour period at a temperature of 55° C. in an amount between 1.03 to 1.05 times the theoretical amount needed to convert the bisphenol-A to tetrabromobisphenol-A.

Methyl bromide was produced during the entire bisphenol-A bromination process. After the bromine addition was completed, the system was held at reflux for 135 minutes to produce additonal methyl bromide and it was distilled out of the reaction mixture. Heating was stopped and 800 parts of water was added over a 30 minute period to precipitate the TBBPA. The reaction medium was then cooled to 30°-40° C. and TBBPA product was removed by filtration.

The filtrate was neutralized with NaOH to a pH of 12-13 and then distilled to remove methanol. The resulting distillation column bottoms contained 1.3 weight percent sodium salts of tribromophenol, 0.5 weight percent sodium salts of tetrabromobisphenol-A, 0.2 weight percent sodium salts of other brominated phenolics, 0.1 weight percent NaOH and about 6 weight percent NaBr.

Polymerization

The above distillation column bottoms were mixed with caustic and chlorine in an approximate 2:1 mole ratio and in an amount which provided the equivalent of 0.5 parts of NaOCl per part of brominated phenolic contaminant in the column bottoms. A solid precipitate formed. After several minutes of standing the solids were filtered and removed. The filtrate was analyzed and found to have non-detectable levels of residual brominated phenolic compounds. Alternatively, the chlorine and caustic can be pre-mixed to form an aqueous NaOCl solution which can be mixed with the column bottoms.

EXAMPLE 2

To 100 parts of an anhydrous methanol solution containing 1.5 weight percent tetrabromobisphenol-A and 1.5 weight percent tribromophenol was added 100 parts of an aqueous 3 weight percent NaOCl solution. This gave a ratio of 1 part NaOCl per part of brominated phenolic compounds. Upon initial contact, the NaOCl and methanol solution formed a homogeneous mixture. After about 10 to 15 seconds solids began to precipitate. The reaction mixture was agitated for approximately 10 minutes. During this time the pH of the system was checked to verify that the mixture was in the range of about 8 to 12. The solids were separated by filtration. The filtrate was found to have negligible levels of residual brominated phenolic compounds. The solids formed had an infrared spectra and average molecular weight similar to the solids formed using an aqueous medium.

EXAMPLE 3

Distillation column bottoms from a tetrabromobisphenol-A process as described in Example 1 were treated at room temperature to determine the reaction time for the polymerization reaction in a batch system. A 100 part sample of distillation column bottoms which contained about 1% brominated phenolics was adjusted to a pH of 11 with NaOH and mixed with an aqueous NaOCl solution at the ratio of 0.35 parts NaOCl/part brominated phenolics. Immediately after mixing, a small aliquot of the mixture was poured into a Buchner funnel and filtered into a CH₃OH—HCl solution. The HCl was used to stop the polymerization reaction and the CH₃OH was used to maintain in solution any unreacted brominated phenolics which tended to precipitate upon acidification. Another small aliquot was filtered into a new CH₃OH—HCl solution after 15 seconds. This procedure was repeated to give a total of 1 minute reaction time.

The first aliquot taken with a reaction time of 0-15 seconds showed a small amount of polymer precipitating in the CH₃OH—HCl solution. Aliquots with reaction times of 15-30 seconds, 30-45 seconds and 45-60 seconds showed no polymer precipitation in the CH₃OH—HCl solution. Analyses of these samples by high pressure liquid chromatography showed no residual brominated phenolics in any of the samples. Thus, the polymerization was substantially complete within 15 seconds.

EXAMPLE 4

Example 3 was repeated using distillation column bottoms containing 1 weight percent brominated phenolics and sufficient NaOH to give an initial pH of 13-14. Aliquots were taken every minute for a total of 10 minutes and filtered into a CH₃OH—HCl solution. A ratio of 0.38 part NaOCl/part brominated phenolics was used in this experiment. Table 2 shows no variation in the concentration of residual organic bromides between aliquot 2 at time 0-30 seconds and aliquot 7 after 10 minutes of reaction. The results indicate that the disappearance of brominated phenolics is as fast at a pH of 13-14 as it is at a pH of 11 as shown in Example 3. However, the fact that residual brominated phenolics remained unreacted indicates that more NaOCl is required for a pH 13-14 system than for a pH 11 system.

TABLE 2

| Time min | Initial pH | Residual Organic bromides (wt %) |
|---|---|---|
| 0 | 13-14 | 1.0 |
| 0-0.5 | 13-14 | 0.34 |

TABLE 2-continued

| Time min | Initial pH | Residual Organic bromides (wt %) |
|---|---|---|
| 1 | 13-14 | 0.34 |
| 2 | 13-14 | 0.33 |
| 3 | 13-14 | 0.31 |
| 4 | 13-14 | 0.31 |
| 5 | 13-14 | 0.31 |

EXAMPLE 5

A series of batch experiments were conducted to determine the effect of temperature on the amount of NaOCl required to polymerize brominated phenolics. In the first experiment a 100 g sample of distillation column bottoms containing approximately 1 weight percent brominated phenolics with an initial pH of 12 was charged to a batch reactor. A 0.3 g charge of NaOH was added to obtain a ratio of NaOCl to brominated phenolics of 0.3:1.0. The reactor was heated to 100° F. and 0.32 g of chlorine was sparged in to form the NaOCl in situ. This slight excess of chlorine brought the pH down to 9. A 10 g sample was then taken from the reactor and analyzed for residual brominated phenolics. A trace of unreacted brominated phenolics was found so 0.1 g of NaOH was added and 0.09 g of chlorine were sparged in to increase the weight ratio of NaOCl to brominated phenolics to 0.4:1.0. Another 10 g sample was analyzed and it was found to be free of brominated phenolics. This test was repeated at different temperatures. Each time excess chlorine was added to control the final pH between 8 and 10. It was found that the amount of NaOCl required increases with temperature. Table 3 shows the effect of temperature on the NaOCl requirements.

More caustic is needed at higher temperatures. At 100° F. the stoichiometric ratio of NaOH to chlorine i.e., 1.13:1.0 gives good results. Approximately 22% more NaOH is needed at 125° F. and 27% more is needed at 160° F.

TABLE 3

| Temp °F. | NaOCl Ratio (Cl$_2$ basis:parts NaOCl/part phenolic) | NaOCl Ratio (NaOH basis:parts NaOCl/part phenolic) |
|---|---|---|
| 100 | 0.4 | 0.4 |
| 125 | 0.45 | 0.55 |
| 160 | 0.59 | 0.75 |

EXAMPLE 6

A series of batch experiments were carried out to determine the effect of pH on the polymerization of brominated phenolics. A 12-inch diameter glass reactor equipped with an agitator and a chlorine sparger was used. It was charged with 50 lbs of column bottoms containing 10,000 ppm of organic bromides. The column bottoms were pretreated with NaOH to a pH of 12. In the first experiment, the temperature of the reactor was set at 85° F. and 0.16 lbs of NaOH was charged to give a NaOCl/organic bromide ratio of 0.3. Then 0.16 lbs of chlorine was sparged into the reactor over a 15 minute period to form the NaOCl in situ and lower the pH to 11. After stirring for 5 more minutes a small sample was analyzed for soluble organic bromides. A trace was found which later analysis by high pressure liquid chromatography showed to be 70 ppm. Another charge of 0.027 lbs of NaOH was made to bring the NaOCl/organic bromide ratio to 0.35. Then 0.024 lbs of chlorine was sparged in over a 2 minute period. The reactor was stirred for 5 minutes and another sample was taken. This sample was found to be free of soluble organic bromides. In following runs the amount of excess chlorine was controlled to vary the pH in the reactor. The data from this series of experiments is given in Table 4. It shows that the weight ratio of NaOCl/brominated phenolics needed to completely destroy the brominated phenolics is greater at high pH. Typically, there is slower polymer formation and growth and delayed precipitation at pH values about 12. The pH in the system was controlled in the range of 7 to 12 to allow complete destruction of brominated phenolics and rapid polymer formation and precipitation. The high end of the range given above is based on the experiments in Table 4. Qualitative observations were made to select pH 7 as the lower end of the preferred range. Maintaining the pH in this range will also reduce the quantity of chlorine and NaOH needed in the reaction to make NaOCl.

TABLE 4

Residual Organic Bromides in ppm vs. NaOCl Utilization and pH of Feed
T = 85° F.

| Ratio[1] | pH = 11 | pH = 12 | pH = 13 | pH = 14 |
|---|---|---|---|---|
| 0.0 | 10,000 | 10,000 | 10,000 | 10,000 |
| 0.3 | 70 | 1,300 | — | — |
| 0.35 | <10 | — | — | — |
| 0.40 | — | 100 | — | — |
| 0.50 | — | <10 | 840 | — |
| 0.75 | — | — | <10 | — |
| 1.0 | — | — | — | 530 |
| 1.25 | — | — | — | <10 |

[1]Weight ratio of NaOCl/organic bromide

We claim:

1. A process for forming a substantially insoluble solid polymer from halogenated phenolic compounds dissolved in a liquid medium, said liquid medium having a pH within the range of 7–14, said process comprising:
    (a) adding an oxidizing agent to said liquid medium containing dissolved polyhalogenated phenolic compounds in an amount sufficient to polymerize said polyhalogenated phenolic compounds to form said solid polymer, and
    (b) reacting at a temperature of about 30° F. to about 300° F.

2. A process of claim 1 wherein said halogenated phenolic compound is a brominated phenolic compound.

3. A process of claim 2 wherein said liquid medium is aqueous.

4. A process of claim 3 wherein said liquid medium has a pH within the range of 8–12.

5. A process of claim 4 wherein said liquid medium has a pH within the range of 9–11.

6. A process of claim 4 wherein said oxidizing agent is an alkali metal hydroxide in combination with a halogen selected from the group consisting of chlorine, bromine and mixtures thereof.

7. A process of claim 6 wherein said oxidizing agent is NaOCl.

8. A process of claim 6 wherein said oxidizing agent is NaOBr.

9. A process of claim 6 wherein said oxidizing agent is the combination of NaOH and chlorine which forms NaOCl.

10. A process of claim 9 wherein said brominated phenolic comounds are selected from the group consisting of tetrabromobisphenol-A, tribromophenol and mixtures thereof.

11. A process of claim 7 wherein said NaOCl is in an amount of about 0.06 to about 10.0 parts by weight of NaOCl for each part by weight of said brominated phenolic compounds.

12. A process of claim 11 wherein said NaOCl is in an amount of about 0.1 to about 1.0 part by weight of NaOCl for each part by weight of said brominated phenolic compounds.

13. A process of claim 12 wherein said NaOCl is in an amount of about 0.35 to about 0.75 part by weight of NaOCl for each part by weight of said brominated phenolic compounds.

14. A process of claim 13 wherein said temperature ranges from about 70° F. to about 110° F.

15. A process for removing halogented phenolic compounds from a liquid medium, said liquid medium having a pH within the range of 7-14, said process comprising:
(a) adding an oxidizing agent to said liquid medium,
(b) reacting at a temperature of 30° F. to 300° F. for sufficient time to polymerize said halogenated phenolic compounds to form a solid polymer and
(c) separating said solid polymer from said liquid medium.

16. In a process for making tetrabromobisphenol-A, said process comprising:
(a) dissolving bisphenol-A in methanol,
(b) adding bromine to the methanol in an amount sufficient to convert said bisphenol-A to tetrabromobisphenol-A,
(c) adding water in an amount sufficient to precipitate said tetrabromobisphenol-A,
(d) separating the precipitated tetrabromobisphenol-A from the reaction mixture,
(e) adding an alkali metal hydroxide to the remaining liquid phase in an amount sufficient to at least neutralize said liquid,
(f) distilling said liquid phase to remove a substantial portion of said methanol, thereby obtaining distillation column bottoms containing minor amounts of dissolved brominated phenolic contaminants, and adjusting the pH of said distillation column bottoms if necessary to be in the range of about 7-14:
the improvement whereby said contaminants are converted to an insoluble solid polymer by polymerizing said contaminants by a procedure comprising adding an oxidizing agent selected from the group consisting of alkali metal hypochlorites, alkali metal hypobromites and the combination of alkali metal hydroxide and halogen selected from chlorine and bromine and mixtures thereof in an amount sufficient to convert said brominated phenolic contaminants to said insoluble solid polymer at a temperature of about 30° F. to about 300° F.

17. A process of claim 16 wherein said oxidizing agent is NaOCl or the combination of NaOH and chlorine and the amount is sufficient to provide about 0.05-10 parts by weight of said oxidizing agent for each part by weight of said brominated phenolic contaminant.

18. A process of claim 17 wherein the pH of said distillate column bottoms is adjusted to be in the range of about 8-12.

19. A process of claim 18 wherein the pH of said distillation column bottoms is adjusted to be in the range of about 9-11.

20. A process of claim 16 wherein said insoluble solid polymer is separated from said distillation column bottoms.

21. In a process for making tetrabromobisphenol-A, said process comprising:
(a) dissolving bisphenol-A in methanol,
(b) adding bromine to the methanol in an amount sufficient to convert said bisphenol-A to tetrabromobisphenol-A,
(c) adding water in an amount sufficient to precipitate said tetrabromobisphenol-A,
(d) separating the precipitated tetrabromobisphenol-A from the reaction mixture,
(e) distilling the remaining liquid phase to remove a substantial portion of said methanol thereby obtaining distillation column bottoms containing minor amounts of dissolved brominated phenolic contaminants, and adjusting the pH of said column bottoms to be in the range of 7-14;
the improvement whereby said contaminants are converted to an insoluble solid polymer by polymerizing said contaminants by a procedure comprising adding an oxidizing agent selected from the group consisting of alkali metal hypochlorites, alkali metal hypobromites and the combination of alkali metal hydroxide and halogen selected from chlorine, bromine and mixtures thereof in an amount sufficient to convert said brominated phenolic contaminants to said insoluble solid polymer at a temperature of about 30° F. to about 300° F.

22. A process of claim 21 wherein said oxidizing agent is an aqueous solution of NaOCl containing excess caustic or the combination of NaOH and chlorine and the amount is sufficient to provide about 0.05-10 parts by weight of said oxidizing agent for each part by weight of said brominated phenolic contaminant.

23. A process of claim 22 wherein the pH of said distillation column bottoms is adjusted to be in the range of 8-12.

24. A process of claim 23 wherein the pH of said distillation column bottoms is adjusted to be in the range of 9-11.

25. A process of claim 21 wherein said insoluble solid polymer is separated from said distillation column bottoms.

26. In a process for making tetrabromobisphenol-A, said process comprising:
(a) dissolving bisphenol-A in methanol,
(b) adding bromine to the methanol in an amount sufficient to convert said bisphenol-A to tetrabromobisphenol-A,
(c) adding water in an amount sufficient to precipitate said tetrabromobisphenol-A,
(d) separating the precipitated tetrabromobisphenol-A from the reaction mixture,
(e) distilling most of the methanol from the remaining liquid phase causing most of the brominated phenolics to precipitate and
(f) separating the precipitated brominated phenolics; the improvement whereby said brominated phenolics are converted to an insoluble polymer by polymerizing said brominated phenolics by a procedure comprising dissolving said brominated phenolics in methanol to form a methanol solution, adjusting the alkalinity so as to be equivalent to about $10^{-7}$ to about $10^{-1}$ weight percent NaOH and adding to said methanol solution an oxidizing agent selected from the group consisting of alkali metal hypochlorites, alkali metal hypobromites, and the combination of alkali metal hydroxide and halogen selected from chlorine, bromine and mixtures thereof in an amount sufficient to convert said brominated phenolics to said insoluble polymer at a temperature of about 30° F. to about 300° F.

27. A process of claim 26 wherein said oxidizing agent is an aqueous solution of NaOCl containing excess caustic or the combination of NaOH and chlorine and the amount is sufficient to provide about 0.05-10 parts by weight of said oxidizing agent for each part by weight of said brominated phenolic.

28. A process of claim 26 wherein the alkalinity of said methanol solution is adjusted to be equivalent to about $10^{-6}$ to about $10^{-2}$ weight percent NaOH.

29. A process of claim 28 wherein the alkalinity of said methanol solution is adjusted to be equivalent to about $10^{-5}$ to about $10^{-3}$ weight percent NaOH.

* * * * *

UNITED STATES PATENT AND TRADEMARK OFFICE
CERTIFICATE OF CORRECTION

PATENT NO. : 4,431,847
DATED : FEBRUARY 14, 1984
INVENTOR(S) : JOSEPH A. BOSSIER, ET AL.

It is certified that error appears in the above-identified patent and that said Letters Patent is hereby corrected as shown below:

Column 1, line 19, reads "TBBA" and should read -- TBBPA --.

Column 1, line 61, reads "compound, weight" and should read -- compound, 3.0-5.0 weight --.

Column 4, line 22, reads "NaOCl, KOBr" and should read -- NaOCl, KOCl, KOBr --.

Column 5, line 42, reads "100°O F" and should read -- 100°F --.

Signed and Sealed this

Eighth Day of May 1984

[SEAL]

Attest:

Attesting Officer

GERALD J. MOSSINGHOFF
Commissioner of Patents and Trademarks